United States Patent
Li et al.

(10) Patent No.: US 9,773,953 B2
(45) Date of Patent: Sep. 26, 2017

(54) ORGANIC PHOSPHOR-FUNCTIONALIZED NANOPARTICLES AND COMPOSITIONS COMPRISING THE SAME

(71) Applicants: RENSSELAER POLYTECHNIC INSTITUTE, Troy, NY (US); UNIVERSITY OF SOUTH CAROLINA, Columbia, SC (US)

(72) Inventors: Ying Li, Troy, NY (US); Peng Tao, Midland, MI (US); Linda S. Schadler, Niskayuna, NY (US); Robert F. Karlicek, Jr., Mechanicville, NY (US); Richard W. Siegel, Menands, NY (US); Lei Wang, Columbia, SC (US); Brian C. Benicewicz, Columbia, SC (US)

(73) Assignee: Rensselaer Polytechnic Institute, Troy, NY (US)

( * ) Notice: Subject to any disclaimer, the term of this patent is extended or adjusted under 35 U.S.C. 154(b) by 195 days.

(21) Appl. No.: 14/781,481

(22) PCT Filed: Apr. 1, 2014

(86) PCT No.: PCT/US2014/032531
§ 371 (c)(1),
(2) Date: Sep. 30, 2015

(87) PCT Pub. No.: WO2014/165516
PCT Pub. Date: Oct. 9, 2014

(65) Prior Publication Data
US 2016/0049559 A1     Feb. 18, 2016

Related U.S. Application Data

(60) Provisional application No. 61/807,111, filed on Apr. 1, 2013.

(51) Int. Cl.
*C08G 79/02*     (2016.01)
*H01L 33/50*     (2010.01)
(Continued)

(52) U.S. Cl.
CPC ............ *H01L 33/504* (2013.01); *B82Y 30/00* (2013.01); *C07F 7/10* (2013.01); *C08G 79/02* (2013.01);
(Continued)

(58) Field of Classification Search
CPC ....... C09K 11/025; C09K 11/02; C09K 11/06; C09K 2211/1011; C09K 2211/1048; H01L 33/504; H01L 33/56; B82Y 30/00
See application file for complete search history.

(56) References Cited

U.S. PATENT DOCUMENTS 7,090,721 B2    8/2006    Craig et al.
7,226,966 B2    6/2007    Kambe et al.
(Continued)

FOREIGN PATENT DOCUMENTS

WO    2009151143 A1    12/2009
WO    2012/037667 A1    3/2012

OTHER PUBLICATIONS

Tsyalkovsky et al, "Fluorescent Nanoparticles Stabilized by Poly-(ethylene glycol) Containing Shell for pH-Triggered Tunable Aggregation in Aqueous Environment", Langmuir, 26(13), May 12, 2010, pp. 10684-10692.*
(Continued)

*Primary Examiner* — Carol M Koslow
(74) *Attorney, Agent, or Firm* — Heslin Rothenberg Farley & Mesit

(57) ABSTRACT

Provided is a phosphor-functionalized nanoparticle that includes an inorganic nanoparticle core; surface polymer brushes that include a plurality of long-chain polymers
(Continued)

bonded to the surface of the inorganic nanoparticle core, said long-chain polymers each having molecular weight greater than 500, and a plurality of short-chain polymers bonded to the surface of the inorganic nanoparticle core, said short-chain polymers each having molecular weight less than 0.5 times the average molecular weight of the long-chain polymers; and one or more organic phosphors bonded to at least one of the inorganic nanoparticle core and one or more of the plurality of short-chain polymers. Graft density of the short-chain polymers on the surface of the inorganic nanoparticle core ($\sigma_{SC}$) is greater than graft density of the long-chain polymers on the surface of the inorganic nanoparticle core ($\sigma_{LC}$). Also provided are polymer matrices, LED's, optical systems, lighting devices, and fixtures that include the inventive nanoparticle.

20 Claims, 5 Drawing Sheets

(51) Int. Cl.
| C07F 7/10 | (2006.01) |
| C09K 11/02 | (2006.01) |
| C09K 11/06 | (2006.01) |
| H01L 33/56 | (2010.01) |
| B82Y 30/00 | (2011.01) |

(52) U.S. Cl.
CPC .......... *C09K 11/02* (2013.01); *C09K 11/025* (2013.01); *C09K 11/06* (2013.01); *H01L 33/56* (2013.01); *C09K 2211/1011* (2013.01); *C09K 2211/1048* (2013.01)

(56) References Cited

U.S. PATENT DOCUMENTS

| 7,259,400 | B1 | 8/2007 | Taskar |
| 7,524,746 | B2 | 4/2009 | Locascio et al. |
| 7,758,928 | B2 | 7/2010 | Bunce et al. |
| 8,035,236 | B2 | 10/2011 | Hawker et al. |
| 8,187,726 | B2 | 5/2012 | Sasaki et al. |
| 8,314,176 | B2 | 11/2012 | Du et al. |
| 8,323,594 | B2 | 12/2012 | Schutte et al. |
| 8,592,037 | B2 | 11/2013 | Parce et al. |
| 8,629,222 | B2 | 1/2014 | Takizawa et al. |
| 2007/0215837 | A1 | 9/2007 | Chiruvolu et al. |
| 2007/0221939 | A1 | 9/2007 | Taskar et al. |
| 2010/0029952 | A1 | 2/2010 | Tweg et al. |
| 2010/0261808 | A1 | 10/2010 | Schadler et al. |
| 2010/0291374 | A1 | 11/2010 | Akarsu et al. |
| 2011/0061891 | A1 | 3/2011 | Schadler et al. |
| 2012/0025216 | A1 | 2/2012 | Kolodin et al. |
| 2012/0126274 | A1 | 5/2012 | Jagt et al. |
| 2013/0116362 | A1 | 5/2013 | Yamazaki et al. |
| 2014/0008697 | A1 | 1/2014 | Harkness et al. |
| 2014/0009964 | A1 | 1/2014 | Dubrow et al. |
| 2014/0071653 | A1 | 3/2014 | Thompson et al. |

OTHER PUBLICATIONS

Li, et al; "Bimodal Surface Ligand Engineering: The Key to Tunable Composites," Langmuir, Oct. 23, 2012, pp. 1211-1220, vol. 29.

Li, et al; "Bimodal Surface Ligand Engineering: The Key to Tunable Composites: Supporting Information," Langmuir, Oct. 23, 2012, vol. 29.

Wong, et al; "Synthesis and Fabrication of Multifunctional Nanocomposites: Stable Dispersions of Nanoparticles Tethered with Short, Dense and Polydisperse Polymer Brushes in Poly(methyl methacrylate)," Advanced Functional Materials, pp. 3614-3624, vol. 22 (2012).

International Search Report and Written Opinion for PCT/US2014/032531 dated Jul. 28, 2014.

Li, et al; "Coumarin-Derived Fluorescent Chemosensors," Advances in Chemical Sensors (2012), InTech, Available from: http://www.intechopen.com/books/advances-in-chemical-sensors/coumarin-derived-fluorescent-chemosensors.

Oikawa, et al; "New Class Materials of Organic-Inorganic Hybridized Nanocrystals/Nanoparticles, and Their Assembled Micro- and Nano-Structure Toward Photonics," Advanced Polymer Science, Oct. 22, 2009, pp. 147-190, vol. 231.

Tao, et al; "Transparent dispensible high-refractive index ZrO2/epoxy nanocomposites for LED encapsulation," Journal of Applied Polymer Science, Dec. 5, 2013, pp. 3785-3793, vol. 130, No. 5.

Extended European Search Report and Search Opinion, mailed on Dec. 19, 2016.

Tsyalkovsky, V., et al., "Fluorescent Reactive Core-Shell Composite Nanoparticles with a High Surface Concentration of Epoxy Functionalities", Chem. Mater., vol. 20, No. 1, pp. 317-325 (2008).

Tsyalkovsky, V., et al., "Fluorescent Nanoparticles Stabilized by Poly(ethylene glycol) Containing Shell for pH-Triggered Tunable Aggregation in Aqueous Environment", Langmuir, vol. 26, No. 13, pp. 10684-10692 (2010).

Wu, T., et al., "Fabrication of Photoswitchable and Thermotunable Multicolor Fluorescent Hybrid Silica Nanoparticles Coated with Dye-Labeled Poly(N-isopropylacrylamide) Brushes", vol. 21, No. 16, pp. 3788-3798 (2009).

Tao, P., et al., "Transparent luminescent silicone nanocomposites filled with bimodal PDMS-brush-grafted CdSe quantum dots", J. Mater. Chem., vol. 1, pp. 86-94 (2013).

Li, G., et al., "Hairy Hybrid Nanoparticles of Magnetic Core, Fluorescent Silica Shell, and Functional Polymer Brushes", Macromolecules, vol. 42, No. 21, pp. 8561-8565 (2009).

Hu, M., et al., "A Sensitive Probe for Determination of $Cu^{2+}$ With Optical Detection in Aqueous Solution", Chinese Journal of Analytical Chemistry, vol. 39, No. 8, pp. 1195-1200, English Abstract (2011).

Shiyong, L., "Design Synthesis and Supramolecular Assembly of Non-linear Reactive Polymers", National Polymeric Academic Paper Report, English Abstract (2011).

\* cited by examiner

ORGANIC PHOSPHOR-FUNCTIONALIZED NANOPARTICLES AND COMPOSITIONS COMPRISING THE SAME

CROSS-REFERENCE TO RELATED APPLICATIONS

This application is a national stage filing under section 371 of International Application No. PCT/US2014/032531, filed on Apr. 1, 2014, and published in English on Oct. 9,2014 as WO 2014/165516 A1, and claims priority to U.S. Provisional Application No. 61/807,111, filed on Apr. 1, 2013. The entire disclosures of each of the prior applications are hereby incorporated herein by reference.

GOVERNMENT RIGHTS STATEMENT

This invention was made with U.S. Government support under EEC-0812056 awarded by the National Science Foundation, and under DMR-0642573 awarded by the National Science Foundation. The U.S. Government has certain rights in the invention.

FIELD OF THE INVENTION

The present invention generally relates to nanoparticles, and more particularly, to phosphor-functionalized nanoparticles and to polymer matrices and optical systems and products incorporating the same.

BACKGROUND OF THE INVENTION

Many superior characteristics of white light-emitting diodes (LEDs) such as high efficiency, low energy-consumption, long lifetime, and excellent reliability have been promoting their penetration into the market for large size flat panel backlighting, street lighting, and museum and residential illuminations. The most commonly used method to generate white light is combining a semiconductor chip emitting at a short wavelength (blue, violet or ultraviolet) with a wavelength converting phosphor which absorbs a portion of light emitted from the diode and undergoes secondary emission at a longer wavelength. Conventional phosphors are composed of an inorganic host substance, such as yttrium aluminum garnet (YAG), containing an optically active dopant which is usually one of the rare-earth elements or a rare-earth compound. The application of the inorganic phosphors is often limited by the resource depletion of rare-earth elements, difficulty in color tuning, and non-uniform dispersion within polymer resins. Typically, inorganic phosphors are mixed in the form of powders with resin, and scattering leads to significantly reduced optical efficiency.

Thus, in order to improve the performance of high brightness white LEDs in terms of higher luminous efficiency and better color rendering ability, highly transparent and efficient light conversion materials are urgently needed.

While certain aspects of conventional technologies have been discussed to facilitate disclosure of the invention, Applicants in no way disclaim these technical aspects, and it is contemplated that the claimed invention may encompass one or more of the conventional technical aspects discussed herein.

In this specification, where a document, act or item of knowledge is referred to or discussed, this reference or discussion is not an admission that the document, act or item of knowledge or any combination thereof was, at the priority date, publicly available, known to the public, part of common general knowledge, or otherwise constitutes prior art under the applicable statutory provisions; or is known to be relevant to an attempt to solve any problem with which this specification is concerned.

SUMMARY OF THE INVENTION

Briefly, the present invention satisfies the need for compositions that afford improved optical systems and products (e.g., LEDs) including the same. The present invention may address one or more of the problems and deficiencies of the art discussed above. However, it is contemplated that the invention may prove useful in addressing other problems and deficiencies in a number of technical areas. Therefore, the claimed invention should not necessarily be construed as limited to addressing any of the particular problems or deficiencies discussed herein.

In one aspect, the invention provides a phosphor-functionalized nanoparticle that comprises:
    an inorganic nanoparticle core;
    surface polymer brushes, including:
        a plurality of long-chain polymers bonded to the surface of the inorganic nanoparticle core, said long-chain polymers each having molecular weight greater than 500; and
        a plurality of short-chain polymers bonded to the surface of the inorganic nanoparticle core, said short-chain polymers each having molecular weight less than 0.5 times the average molecular weight of the long-chain polymers; and
    one or more organic phosphors bonded to at least one of the inorganic nanoparticle core and one or more of the plurality of short-chain polymers,
wherein graft density of the short-chain polymers on the surface of the inorganic nanoparticle core ($\sigma_{SC}$) is greater than graft density of the long-chain polymers on the surface of the inorganic nanoparticle core ($\sigma_{LC}$).

In another aspect, the invention provides a polymer matrix comprising the inventive phosphor-functionalized nanoparticle described above.

In another aspect, the invention provides an LED comprising the inventive phosphor-functionalized nanoparticle and/or the inventive polymer matrix.

In another aspect, the invention provides an optical system comprising the inventive nanoparticle and/or polymer matrix.

In another aspect, the invention provides a lighting device comprising the inventive nanoparticle, polymer matrix, and/or optical system.

In another aspect, the invention provides a fixture comprising the inventive nanoparticle, polymer matrix, and/or optical system.

Certain embodiments of the presently-disclosed phosphor-functionalized nanoparticles, polymer matrices, optical systems, and products (e.g., LEDs, lighting devices, fixtures) have several features, no single one of which is solely responsible for their desirable attributes. Without limiting the scope of these phosphor-functionalized nanoparticles, polymer matrices, optical systems, and products (e.g., LEDs, lighting devices, fixtures) as defined by the claims that follow, their more prominent features will now be discussed briefly. After considering this discussion, and particularly after reading the section of this specification entitled "Detailed Description of the Invention," one will understand how the features of the various embodiments disclosed herein provide a number of advantages over the current state of the art. These advantages may include, without limitation, providing improved nanoparticles that are useful in various applications, including, for example, in LEDs and optical systems. The nanoparticles may also allow for improved, highly transparent and efficient light conversion materials. Inventive embodiments provide a method to bind organic phosphors (organic dyes) onto surfaces of inorganic nanoparticles, and/or onto polymers disposed thereon in a controlled manner, and, through the inventive nanoparticles, provide a method and polymer composition/matrix having homogenous dispersion of phosphor functionalized nanoparticles. The incorporation of high refractive index nanoparticles to LED encapsulation polymer materials can lead to higher light extraction efficiency. Meanwhile, the inventive phosphor-functionalized nanoparticles may also act as carriers for additional functionality, such as color conversion and conductivity. In particular embodiments, the invention provides superior control of the spacing, concentration of dyes, grafting densities of the polymers and novel dye chemistries to achieve excellent dispersions of metal oxide nanomaterials.

These and other features and advantages of this invention will become apparent from the following detailed description of the various aspects of the invention taken in conjunction with the appended claims and the accompanying drawings.

BRIEF DESCRIPTION OF THE DRAWINGS

The present invention will hereinafter be described in conjunction with the following drawings.

DETAILED DESCRIPTION OF THE INVENTION

Figure 1:
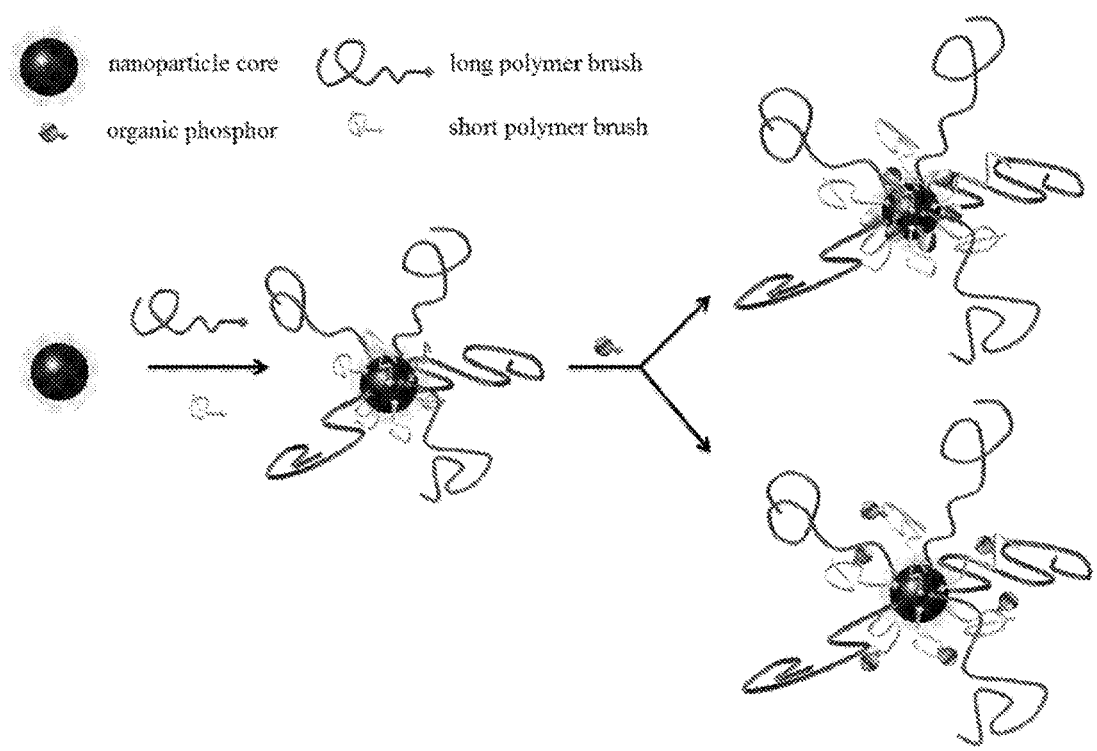
FIG. 1 is a schematic illustration of embodiments of the inventive phosphor-functionalized nanoparticle having attachment of an organic phosphor (fluorescent dye) onto nanoparticles with a bimodal polymer brush design.

Aspects of the present invention and certain features, advantages, and details thereof, are explained more fully below with reference to the non-limiting embodiments illustrated in the accompanying drawings. Descriptions of well-known materials, fabrication tools, processing techniques, etc., are omitted so as to not unnecessarily obscure the invention in detail. It should be understood that the detailed description and the specific examples, while indicating embodiments of the invention, are given by way of illustration only, and are not by way of limitation. Various substitutions, modifications, additions and/or arrangements within the spirit and/or scope of the underlying inventive concepts will be apparent to those skilled in the art from this disclosure. Reference is made below to the drawings, which are not necessarily drawn to scale, and which are provided for ease of understanding.

In one aspect, the invention provides a phosphor-functionalized nanoparticle that comprises:
an inorganic nanoparticle core;
surface polymer brushes, including:
a plurality of long-chain polymers bonded to the surface of the inorganic nanoparticle core, said long-chain polymers each having molecular weight greater than 500; and
a plurality of short-chain polymers bonded to the surface of the inorganic nanoparticle core, said short-chain polymers each having molecular weight less than 0.5 times the average molecular weight of the long-chain polymers; and
one or more organic phosphors bonded to at least one of the inorganic nanoparticle core and one or more of the plurality of short-chain polymers,
wherein graft density of the short-chain polymers on the surface of the inorganic nanoparticle core ($\sigma_{SC}$) is greater than graft density of the long-chain polymers on the surface of the inorganic nanoparticle core ($\sigma_{LC}$).

The inorganic nanoparticle core of the inventive phosphor-functionalized nanoparticle includes any inorganic material or combination of inorganic materials. As used herein, inorganic materials generally exclude organic compounds where carbon is present and is covalently bonded to another atom, although inorganic materials include carbides.

Non-limiting examples of inorganic materials that may be included in the nanoparticle core include materials that comprise a metal or semimetal (including semiconductor) compound with any one or more of oxygen (oxide), nitrogen (nitride), carbon (carbide), sulfur (sulfide), chlorine (chloride), and phosphorous (phosphide).

In some embodiments, the inorganic nanoparticle core comprises a III-N compound, and/or a metal oxide. A "III-N compound" is a compound comprising one or more group III elements from the periodic table (for example, B, Al, Ga, In, Tl), and the element nitrogen (N).

In some embodiments, the inorganic nanoparticle core comprises a metal oxide. For example, in some embodiments, the inorganic nanoparticle includes a metal oxide selected from titanium dioxide ($TiO_2$), indium tin oxide (ITO), and zirconium dioxide ($ZrO_2$). In a particular embodiment, the inorganic nanoparticle core comprises $ZrO_2$.

In some embodiments, the inorganic nanoparticle core has a refractive index greater than 1.90. For example, in some embodiments, the refractive index is 1.95 or more (e.g., 1.95, 2.00, 2.05, 2.10, 2.15, 2.20, 2.25, 2.30, 2.35, 2.40, 2.45, 2.50, 2.55, 2.60, 2.65, 2.70, 2.75, 2.80, 2.85, 2.90, 2.95, or 3.00, including any and all ranges and subranges therein). In some embodiments, the inorganic nanoparticle core has a refractive index from 2.00 to 3.00. In some embodiments, the inorganic nanoparticle core has a refractive index from 1.95 to 2.85.

For the purposes of this disclosure, the term "nanoparticle" is used in a broad sense, though for illustrative purposes only, some typical attributes of nanoparticles suitable for use in this invention are a particle size of 1-100 nanometers including any and all subranges therein, and, with regards to particle shape, an aspect ratio of between 1 and 1,000, including any and all subranges therein (e.g., 1-10).

The phosphor-functionalized nanoparticle of the invention includes surface polymer brushes, which are polymers bonded to the surface of the nanoparticle. The inventive phosphor-functionalized nanoparticle is at least bimodal, meaning that the surface polymer brushes are of at least two different lengths. The surface polymer brushes include, at least, a plurality of long-chain polymers bonded to the surface of the inorganic nanoparticle core, and a plurality of short-chain polymers bonded to the surface of the inorganic nanoparticle core. The long-chain polymers each have a molecular weight greater than 500, and the short-chain polymers each have a molecular weight less than 0.5 times the average molecular weight of the long-chain polymers.

In some embodiments, the long-chain polymers each have a molecular weight of 600 to 100,000. For example, in some embodiments, the long chain polymers may have molecular weights of 600, 700, 800, 900, 1,000, 1,100, 1,200, 1,300, 1,400, 1,500, 1,600, 1,700, 1,800, 1,900, 2,000, 2,100, 2,200, 2,300, 2,400, 2,500, 2,600, 2,700, 2,800, 2,900, 3,000, 4,000, 5,000, 6,000, 7,000, 8,000, 9,000, 10,000, 11,000, 12,000, 13,000, 14,000, 15,000, 16,000, 17,000, 18,000, 19,000, 20,000, 21,000, 22,000, 23,000, 24,000, 25,000, 50,000, 75,000, or 100,000, including any and all ranges and subranges therein (e.g., 1,500-30,000, 600-2,500, 800-1,600, etc.)

In some embodiments, the short-chain polymers have a molecular weight of 150 to 1,000, for example, 150, 200, 250, 300, 350, 400, 450, 500, 550, 600, 650, 700, 750, 800, 850, 900, 950, 1,000, 2,000, 3,000, 4,000, 5,000, 6,000, 7,000, 8,000, 9,000, or 10,000 including any and all ranges and subranges therein (e.g., 150-600, 150-3,500, etc.).

As mentioned above, the phosphor-functionalized nanoparticles of the invention are at least bimodal, that is, they comprise at least long and short-chain polymers (which may also be referred to as long- and short-chain polymer brushes). The polymer brushes may be grafted (bonded) to the inorganic nanoparticle core using any art-acceptable technique. For example, the polymer chains may be bonded to the core using a controlled "grafting-from" polymerization technique such as ATRP (Atom Transfer Radical Polymerization), NMP (Nitroxide-Mediated Radical Polymerization) or RAFT (Reversible Atom Fragmentation Transfer Polymerization). RAFT polymerization is a recently developed controlled rapid polymerization (CRP) technique that may be used to prepare polymer materials with predetermined molecular weights, controlled polydispersities, and advanced architectures.

An alternative approach is an at least two-step "grafting-to" approach where a longer brush is attached in the first "grafting-to" step (thereby resulting in a graft density of the long-chain polymers on the surface of the inorganic nanoparticle core, $\sigma_{LC}$), and a shorter brush then fills in the remaining space on the particle surface at a higher graft density ($\sigma_{SC}$) during an additional "grafting-to" step.

As used herein, "grafting" requires that a polymer chain is bonded to the nanoparticle core. For polymer surface brushes, the long- and short-polymer chains extend distally away from the nanoparticle core, and thus the middle portion of the polymer chain (i.e., the portion comprising the polymer repeating units), and the end group opposite the end grafted to the nanoparticle core, are not in contact with the nanoparticle core. Thus, the polymer surface brushes of the inventive nanoparticle differ from traditional polymer coatings, in which all portions of, or the majority of portions of a polymer chain, would be in contact with the core.

In some embodiments, the short brushes (i.e., the short-chain polymers) are grafted at relatively high graft densities ($\sigma_{SC}$) and enthalpically screen the particle core-core attraction, and the long brushes are sparsely grafted. Such embodiments may, for example, suppress entropic dewetting of high-molecular-weight commercial matrices (e.g., silicone matrices).

In some embodiments, the short-chain polymer graft density ($\sigma_{SC}$) is greater than 2, 3, 4, 5, 6, 7, 8, 9, 10, 11, 12, 13, 14, 15, 16, 17, 18, 19, or 20 times the long-chain polymer graft density ($\sigma_{LC}$).

In some embodiments, the polymer surface brushes (e.g., the long- and/or short-chain polymers) are transparent in a polymer matrix. In some embodiments, the inventive phosphor-functionalized nanoparticles, when dispersed in a polymer matrix (e.g., a matrix in which some or all of the surface brushes are compatible), form part of a polymer matrix composition that has a light transmission of at least 80% at a thickness of 0.5 mm over the visible range of wavelengths.

In some embodiments, the polymer surface brushes (e.g., the long- and/or short-chain polymers, and/or other polymer surface brushes, where present) include units from polymers synthesized using monomers that include methacrylates, styrenes, and/or acrylates.

In some embodiments, the polymer surface brushes (e.g., the long- and/or short-chain polymers, and/or other polymer surface brushes, where present) include poly(glycidyl methacrylate) units, polydimethylsiloxane units, poly(dimethylsiloxane-co-diphenylsiloxane) units, poly(methyl methacrylate) (PMMA) units, cyclo-aliphatic polymer units, polyethylene terephthalate (PET) units, polyethylene naphthalate (PEN) units, and/or poly(methylphenylsiloxane) units. As used herein, the term "units" refers to repeating units of a polymer. A repeating unit is a part of a polymer whose repetition would produce the complete polymer chain (except for the end-groups) by linking the repeat units together successively along the chain.

In some embodiments, the long- and/or short-chain polymers comprise poly(glycidyl methacrylate) units, polydimethylsiloxane units, and/or poly(dimethylsiloxane-co-diphenylsiloxane) units.

In some embodiments, the polymer surface brushes (e.g., one or more of the long- and/or short-chain polymers, or other polymer surface brushes, if present) are copolymers comprising units from at least two different monomers.

In some embodiments of the invention, the short-chain polymers have an average length of 3-20 mers, for example, 3, 4, 5, 6, 7, 8, 9, 10, 11, 12, 13, 14, 15, 16, 17, 18, 19, or 20 mers, including any and all ranges and subranges therein (e.g. 3-15 mers, 5-10 mers, etc.).

In some embodiments of the invention, the long-chain polymers have an average length of 8-80 mers, for example, 8, 10, 15, 20, 25, 30, 35, 40, 45, 50, 55, 60, 65, 70, 75, or 80 mers, including any and all ranges and subranges therein (e.g. 8-60 mers, 10-50 mers, etc.).

In some embodiments, the polymer brushes (e.g., the long- and/or short-chain polymers) are compatible with an intended matrix. For example, in some embodiments, brushes (e.g., the long- and/or short-chain polymers) are epoxy compatible or silicone compatible.

The term "compatible" as used herein means that a polymer (e.g., a polymer brush, such as a long- or short-chain polymer) is chemically similar enough to a polymer matrix that the dispersion of the inventive nanoparticle comprising a compatible polymer meets at least one of the following criteria: a) the largest agglomerates of phosphor-functionalized nanoparticles in a polymer matrix after dispersion and mixing are 500 nm in diameter and at least 50% of the agglomerates have a diameter less than 250 nanometers; b) the largest agglomerates of phosphor-functionalized nanoparticles in the polymer matrix after dispersion and mixing are 100 nanometers in diameter and no more than 50% of the agglomerates are 100 nanometers in diameter; or c) at least 50% of the phosphor-functionalized nanoparticles are individually dispersed in the polymer matrix after dispersion and mixing.

In particular embodiments of the invention, polymer brushes (e.g., long and/or short-chain polymers) and an intended polymer matrix will have identical functionalities, for example, when they are each of the same chemical class.

The inventive phosphor-functionalized nanoparticle includes one or more organic phosphors bonded to at least one of the inorganic nanoparticle core and one or more of the plurality of short-chain polymers.

In some embodiments of the inventive nanoparticle, at least one of the one or more organic phosphors is bonded to the inorganic nanoparticle core.

In some embodiments of the inventive nanoparticle, at least one of the one or more organic phosphors is bonded to one (or more) of the short-chain polymers.

In some embodiments of the inventive nanoparticle, at least one of the one or more organic phosphors is bonded to one (or more) of the short-chain polymers, and at least one of the one or more organic phosphors is bonded to the inorganic nanoparticle core In some embodiments, the organic phosphor molecule(s) is/are covalently bonded to the inorganic nanoparticle core, and/or to one of the short-chain polymers.

In some embodiments of the invention, organic phosphor molecules are bonded (e.g., covalently) to the grafted polymer chain or directly anchored onto the nanoparticle core surface via a facile ligand exchange process.

Figure 3:
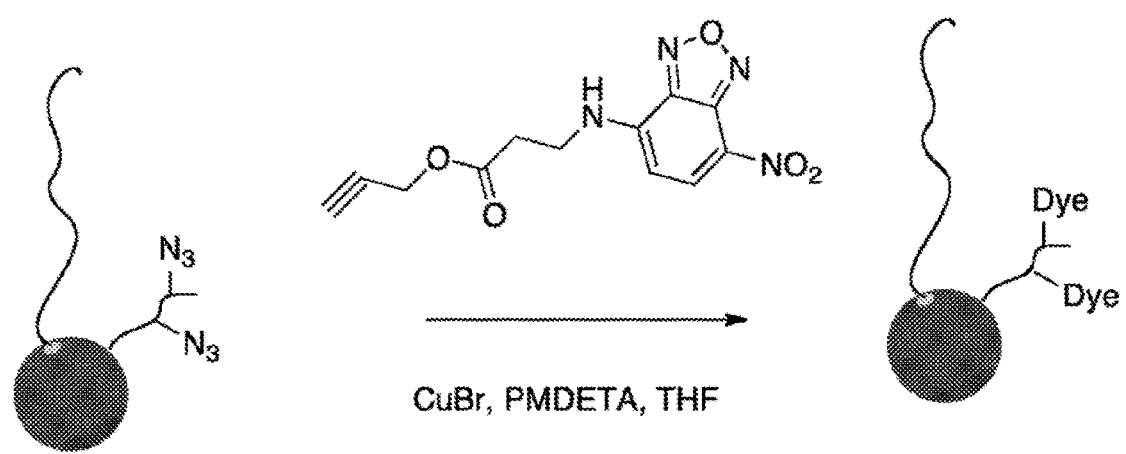
FIG. 3 is an illustration of a bimodal design utilizing the "click" approach to attach alkynyl NBD to short-chain polymers.

Persons having ordinary skill in the art will appreciate that various synthetic routes are available to graft/bond phosphors to the inorganic nanoparticle core and/or to the short-chain polymers. All of such appropriate routes are within the purview of this invention. For example, phosphors containing groups such as alkynyl, carboxylic acid, phosphonate and phosphonic acid groups allow for synthetic variations in the preparation of functionalized nanoparticles. Other than direct attachment to the surface or polymer by a carboxylic acid functionalized dye, methods of functionalizing the nanoparticles with the phosphors/dyes include direct attachment to the surface by a phosphonic acid/phosphonate functionalized dye and clicking alkyne functionalized dyes to an azide functionalized polymer on the nanoparticles. For example, for the phosphonate modified NBD dye shown herein, the modification occurs at reflux in various solvents from temperatures ranging from 70-110° C. In the click approach, which is shown in FIG. 3, and which is described in, e.g., U.S. Application Publication Nos. 2010-0261808-A1 and 2011-0061891-A1, an alkyne modified dye is clicked onto a bimodal polymer brush grafted particle with the short brush chain having an azide moiety. In this approach, the bimodal nature of the nanoparticle allows for tuning both the enthalpic and entropic factors of the interface interaction between inorganic nanofiller and organic matrix.

The bimodal approach provides two ways of controlling the population of dye molecules: (a) the number and spacing of the azide moieties of the short chain/long chain can be varied (b) the grafting density of the azide containing polymer can be varied to adjust its spacing on the nanoparticle surface.

In various embodiments, the at least bimodal surface architecture of the inventive nanoparticle, when dispersed in a polymer matrix, allows the long-chain polymers to both screen the surface of nanoparticle cores from each other and compatibilize the nanoparticles with the polymer matrix. Meanwhile, the intermolecular spacing of organic phosphor molecules on each nanoparticle is related to the graft density of the short brush ($\sigma_{SC}$), which determines the available grafting sites for the attachment of organic phosphor. In some embodiments, the long-chain polymers help screen the fluorescent dyes from the matrix. Thus, in various embodiments, the bimodal design favors good dispersion of nanoparticles in polymer matrices and thereby high transparency of the resultant polymer matrices and nanocomposites.

By varying the graft density of the organic phosphor and surface polymer brushes, including the long- and short-chain polymers, and optionally any other polymer brushes that may be present, and/or by varying the functionalized nanoparticle loading, the photoluminescent property of the inventive phosphor-functionalized nanoparticle can be optimized for, e.g., white LED applications.

As discussed above, in some embodiments the inventive nanoparticle is bimodal. However, in other embodiments, the inventive nanoparticles are multimodal (e.g., trimodal or more), meaning that they may include polymer brushes in addition to the long- and short-chain polymers.

In some embodiments, the surface polymer brushes of the inventive phosphor-functionalized nanoparticle have a polydispersity index (PDI) of at least 1.3. PDI is a measure of the distribution of molecular mass in a given polymer sample. The PDI is the weight average molecular weight ($M_w$) divided by the number average molecular weight ($M_n$). It indicates the distribution of individual molecular masses in a batch of polymers. PDI values for polymers are greater than or equal to 1, but as polymer chains approach uniform chain length, PDI approaches unity (1).

Relatively higher PDI's (e.g., 1.5 and higher) for mixed (e.g., bimodal or multimodal) surface polymer brushes can result in nanoparticles that are capable of improved dispersion (of both nanoparticles themselves and organic phosphors thereon) in polymer matrices. These mixed (multimodal) high PDI brushes are expected to have a balance in enthalpic/entropic interactions with polymer matrix.

In some embodiments, the surface polymer brushes of the inventive phosphor-functionalized nanoparticle have a polydispersity index (PDI) of 1.3 to 3.0, for example, 1.3, 1.4, 1.5, 1.6, 1.7, 1.8, 1.9, 2.0, 2.1, 2.2, 2.3, 2.4, 2.5, 2.6, 2.7, 2.8, 2.9, or 3.0, including any and all ranges and subranges therein (e.g., a PDI of 1.5 to 2.3, or of 1.8 to 2.0, etc.).

A broad range of organic phosphors can be used in the inventive nanoparticle. Persons having ordinary skill in the art will be able to select a desired phosphor based on various criteria, including desired application, and desired excitation and emission wavelengths.

In some embodiments, one or more phosphors comprised by the inventive nanoparticle have an excitation wavelength of, e.g., about 330 nm to about 650 nm.

In some embodiments, one or more phosphors comprised by the inventive nanoparticle have an emission wavelength of, e.g., about 430 nm to about 680 nm.

In some embodiments, the phosphor comprised by the inventive nanoparticle may include one or more of acridine, alizarin, coumarin, astrazon, atabrine, auramine, bodipy, calcein, calcofluor, cascade blue, catecholamine, chinacrine, CY7, DANS (1-DimethylAmino-Naphthaline-5-Sulphonic Acid), DAPI, dimethylamino-5-Sulphonic acid, dopamine, euchrysin, fluorescein, gloxalic acid, haematoporphyrin, 5-hydroxy-tryptamine (5-HT), leucophor, lucifer yellow, LysoTracker, maxilon, mitotracker, NBD, nile red, noradrenaline, phorwite, pyronine, rhodamine, sevron brilliant, thiolyte, Uranine B, TOTO, YOYO and others.

In some embodiments, at least one of the one or more organic phosphors comprises a compound or residue thereof, wherein the compound is selected from fluorescein, a fluorone dye (e.g., rhodamine), an arylsulfonate dye (e.g., pyranine), and a compound containing a residue of Formula (I):

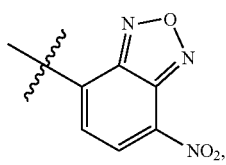

(I)

where the wavy line indicates the point of connection of the residue of Formula (I) to the remainder of the compound that comprises the residue of Formula (I).

For example, each of the following compounds includes the residue of Formula (I), and as such, in some embodiments of the invention, one or more phosphors comprise one of the following compounds, or a residue thereof:

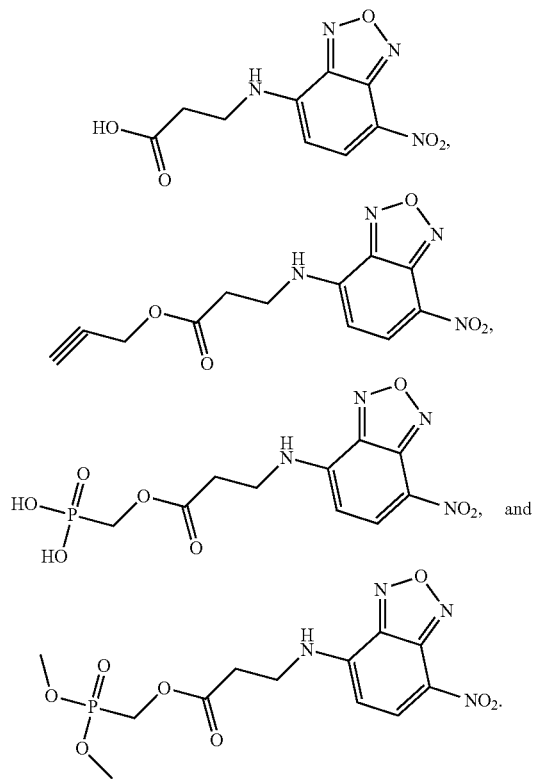

A residue is a recognizable molecular part of a larger molecule. Persons having ordinary skill in the art will appreciate that whether the phosphor comprised in the inventive nanoparticle is a compound as described herein or is a residue thereof will depend upon the nature of the phosphor itself, the surface chemistry of the inorganic nanoparticle core, and the affinity (e.g., bonding) between the two.

In some embodiments of the invention, at least one of the one or more organic phosphors comprises a compound of Formula (II) or a residue thereof:

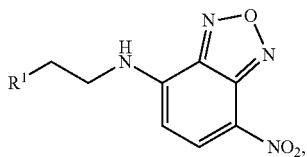

(II)

wherein
$R^1$ is selected from —COOH, —C(O)OCH$_2$CCH, and —C(O)OCP(O)(OR$^{2a}$)(OR$^{2b}$); and
$R^{2a}$ and $R^{2b}$ are individually selected from hydrogen and C$_{1-6}$ alkyl.

The term "alkyl" is intended to include linear, branched, or cyclic hydrocarbon structures and combinations thereof. Examples of alkyl groups include methyl, ethyl, propyl, isopropyl, butyl, s-and t-butyl and the like. Cycloalkyl is a subset of alkyl.

In some embodiments, the organic phosphor of the invention (e.g., a compound according to Formula (I) or residue thereof) absorbs light in the 415-490 nm region. In certain embodiments, the nanoparticle core used together with such phosphors is, for example, a ZrO$_2$ core, having absorption in the 200-360 nm range. When excited at 465 nm by a blue LED, NBD-COOH emits yellow light at 525 nm, enabling its usage as a phosphor for white LED applications.

In some embodiments, one or more phosphor is a coumarin derivative of Formula (III), or a residue thereof:

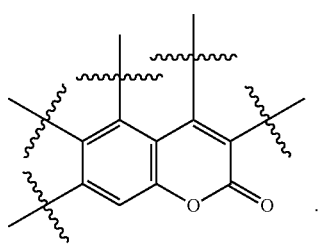

(III)

Some coumarin derivatives are described, for example, in Hongqi Li, Li Cai and Zhen Chen (2012). Coumarin-Derived Fluorescent Chemosensors, Advances in Chemical Sensors, Prof. Wen Wang (Ed.), InTech, Available from: http://www.intechopen.com/books/advances-in-chemical-sensors/coumarin-derived-fluorescent-chemosensors.

FIG. 1 is a schematic illustration of embodiments of the inventive phosphor-functionalized nanoparticle having attachment of an organic phosphor (fluorescent dye) onto nanoparticles with a bimodal polymer brush design. As depicted, the organic phosphor may be bonded to the inorganic nanoparticle core, or to short-chain polymer surface brushes.

In some embodiments of the invention, the functionalization of the nanoparticle core is conducted after the bimodal polymer brush grafting.

In another aspect, the invention provides a polymer matrix comprising the inventive phosphor-functionalized nanoparticle described above.

The amount of phosphor-functionalized nanoparticle present in a given embodiment of the invention, relative to the amount of polymer matrix present, can vary as desired in an application-specific manner. A non-limiting example of amounts of phosphor-functionalized nanoparticle typically present in various embodiments of the invention is a range where the modified nanoparticle volume fraction is between about 0.1 percent and about 25 percent.

In some embodiments of the invention, the phosphor-functionalized nanoparticles are homogenously dispersed throughout the polymer matrix.

In some embodiments, the polymer matrix is transparent, i.e., the matrix has a light transmission of at least 80% at a thickness of 0.5 mm over the visible range of wavelengths.

In some embodiments of the invention, the polymer matrix comprises poly(glycidyl methacrylate), polydimethylsiloxane, poly(dimethylsiloxane-co-diphenylsiloxane), poly(methyl methacrylate) (PMMA), a cyclo-aliphatic polymer, polyethylene terephthalate (PET), polyethylene naphthalate (PEN), and/or poly(methylphenylsiloxane).

In some embodiments, the polymer matrix is epoxy-based (i.e., it comprises epoxy).

In some embodiments, the polymer matrix is silicone-based.

In some embodiments, the polymer matrix includes long chain polymers that are matrix compatible.

In another aspect, the invention provides an LED comprising the inventive phosphor-functionalized nanoparticle and/or the inventive polymer matrix. For example, in some embodiments, an LED comprises a coating (e.g., a conformal coating) of polymer matrix comprising the inventive nanoparticles. In some embodiments, the coating may be, e.g., 5-15 µm thick.

In some embodiments, the invention provides an LED including a polymer matrix that comprises the inventive nanoparticle, and phosphors are homogenously dispersed throughout the polymer matrix.

In another aspect, the invention provides an optical system comprising the inventive nanoparticle and/or polymer matrix.

In another aspect, the invention provides a lighting device comprising the inventive nanoparticle, polymer matrix, and/or optical system.

In another aspect, the invention provides a fixture comprising the inventive nanoparticle, polymer matrix, and/or optical system.

The following are non-limiting examples of embodiments of the present invention.

EXAMPLE 1

Phosphor-Functionalized Nanoparticle

Figure 2A:
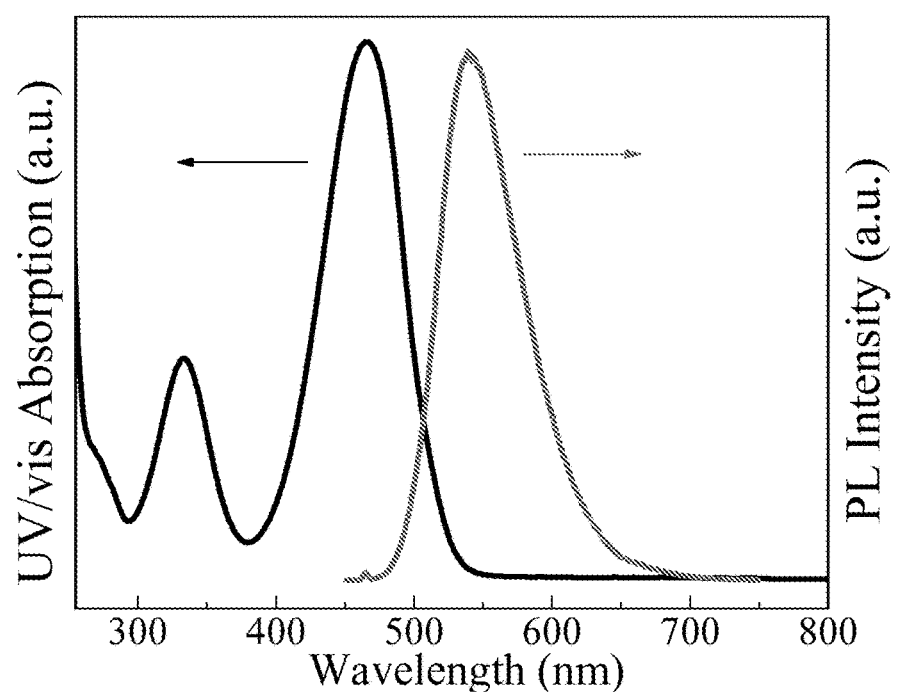
FIG. 2A provides a UV/Vis absorption and PL emission spectra for a NBD-COOH functionalized $ZrO_2$ nanoparticle solution.
Figure 2B:
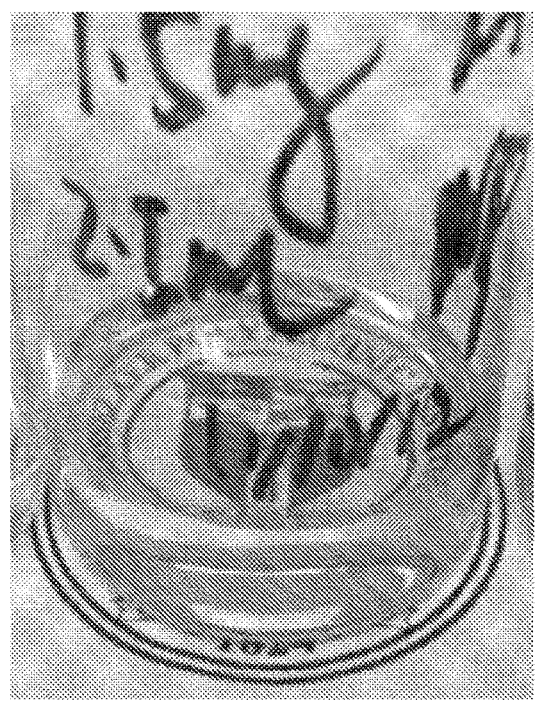
FIG. 2B is a digital photograph of a NBD-COOH functionalized $ZrO_2$ nanoparticle solution.

After polymer grafting of bimodal polydimethylsiloxane (PDMS) silicone long- and short-chain polymers to a $ZrO_2$ nanoparticle core, where the phosphonic acid or carboxylic acid head group of the polymer replaces the weakly bonded capping ligands on the as-synthesized $ZrO_2$ nanoparticle surfaces, the purified nanoparticle solution was mixed with the dye solution at ambient conditions under sonication, and NBD-COOH was attached to the grafted nanoparticles via the coupling of the carboxylic acid head group with the particle surfaces. FIG. 2A provides a UV/Vis absorption and PL emission spectra for a NBD-COOH functionalized $ZrO_2$ nanoparticle solution. FIG. 2B is a digital photograph of a NBD-COOH functionalized $ZrO_2$ nanoparticle solution. As shown in FIGS. 2A-B, the solution absorption and photoluminescence (PL) emission spectra of the functionalized particles are nearly the same as those of the free NBD-COOH, except for the small red-shifted PL spectrum, suggesting that such high refractive index, yellow-emitting nanoparticles would be promising candidates for white light conversion in LEDs.

The transparent yellow chloroform solution for the functionalized nanoparticles shown in FIG. 2B is preliminary evidence of the successful attachment of the dye, which cannot dissolve in chloroform as free molecules. The ligand exchange process and successful incorporation of dye were further confirmed by Thermal Gravimetric Analysis. The dye loadings can be controlled by adjusting the ratio of dye/nanoparticle.

EXAMPLE 2

Polymer Matrix Comprising Phosphor-Functionalized Nanoparticle

To demonstrate the practical value of embodiments of the inventive nanoparticles, the functionalized nanoparticles are dispersed in a silicone matrix at different loadings (1, 3, 5, 7 wt %) to test on a blue LED. The functionalized particle loadings are kept relatively low to maintain reasonable interparticle distance. On the other hand, to obtain the desired refractive index enhancement, grafted nanoparticles without functionalization can be mixed with functionalized particle to increase the particle core loading without reducing the intermolecular distance of dye on neighboring particles.

Figure 4A:
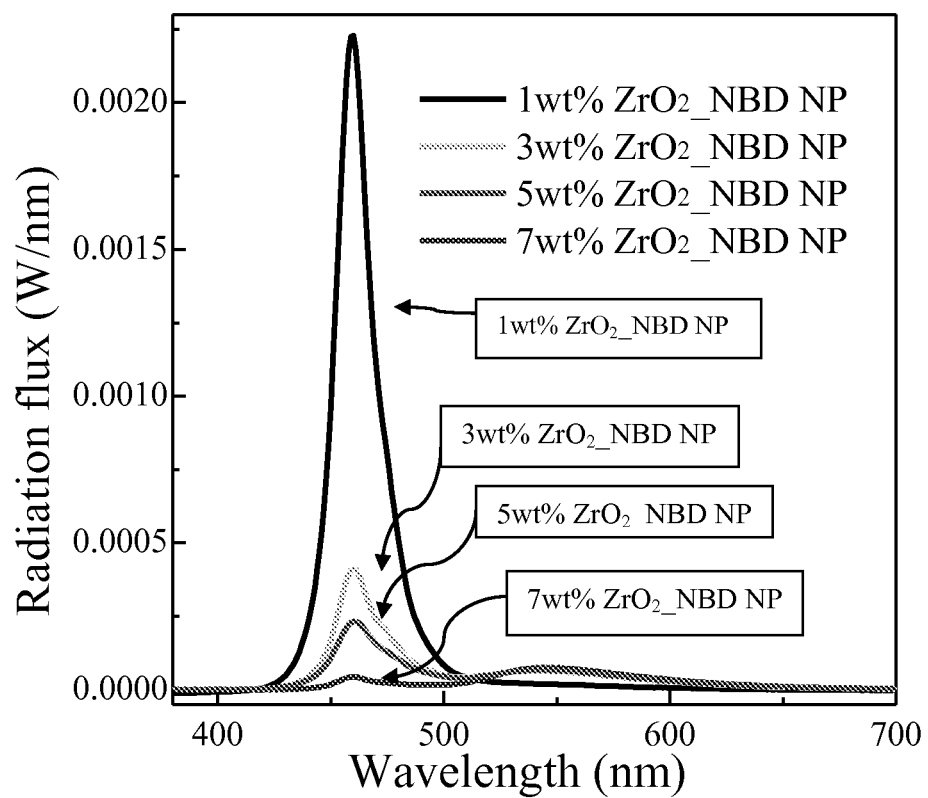
FIG. 4A provides radiation flux curves of a blue-emitting LED coated with silicone nanocomposites containing functionalized nanoparticle at different loadings.
Figure 4B:
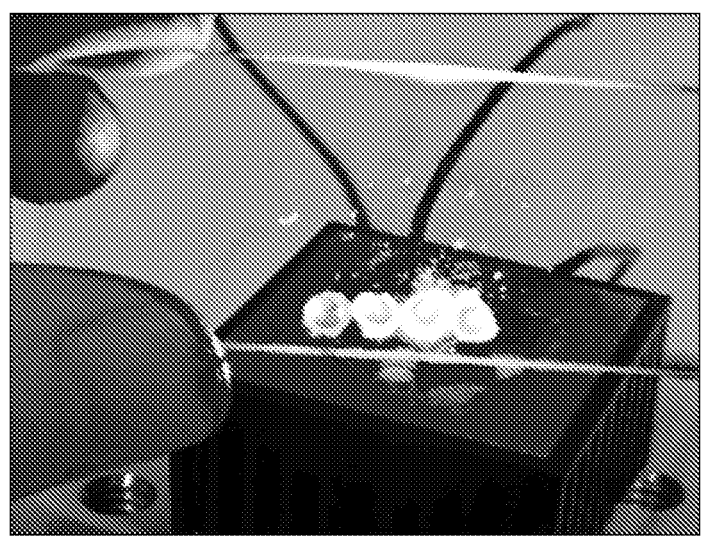
FIG. 4B is a digital photograph that shows the transparent semi-spherical nanocomposite dome.
Figure 5A:
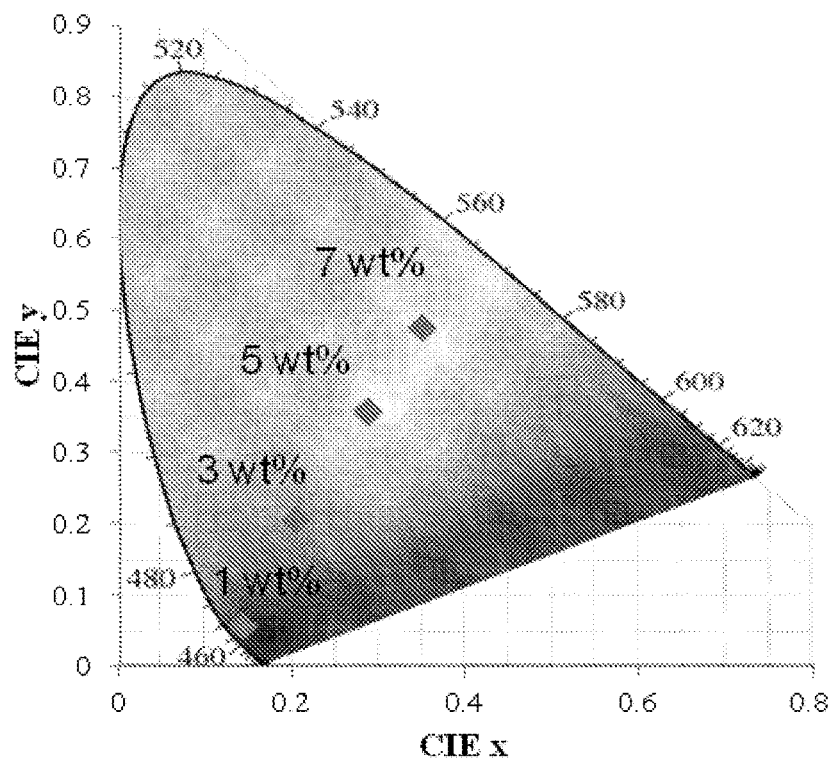
FIGS. 5A-B provide CIE x y coordinates and corresponding digital photographs of a blue-emitting LED coated with silicone nanocomposites (polymer matrices) containing functionalized nanoparticle at different loadings
Figure 5B:
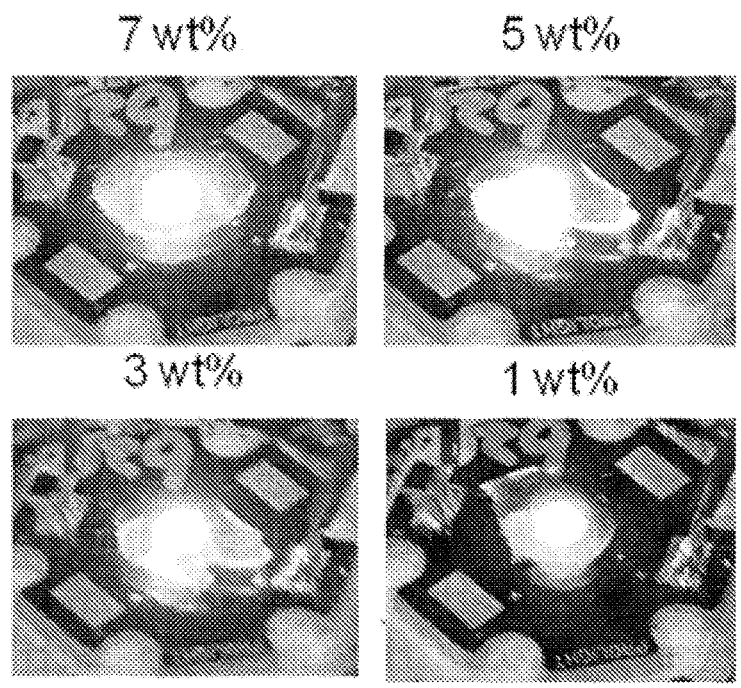

The functionalized nanocomposites are highly transparent in the 550-800 nm wavelength range, indicating homogenous dispersion of functionalized nanoparticles attributable to the bimodal surface modification design. In order to better control the fabrication process of nanocomposite encapsulant material, a Teflon mold was used to prepare hemispherical encapsulant with diameter equals to that of the reflector cup of the LED. As shown in FIGS. 4A-B, the functionalized encapsulant materials absorb blue emission and emit yellow light to a different extent. FIG. 4A provides radiation flux curves of a blue-emitting LED coated with silicone nanocomposites containing functionalized nanoparticles at different loadings. FIG. 4B is a digital photograph that shows the transparent semi-spherical nanocomposite dome. The CIE color space was used to represent the color of the encapsulated LED. The total emission appears to be greenish for the 7 wt % sample while gradually tuning into blue for the 1 wt % sample, as shown in FIGS. 5A-B, which provide CIE x y coordinates and corresponding digital photographs of a blue-emitting LED coated with silicone nanocomposites containing functionalized nanoparticle at different loadings.

A common issue of organic dyes is their finite lifetime. In order to enhance the lifetime and stabilize emission intensity of the anchored dye molecules under strong blue light excitation, the functionalized nanoparticle is coated with a silica ($SiO_2$) shell, which would provide a confined environment and a platform for easy postfunctionalization with powerful $SiO_2$ surface chemistry toolbox. In a typical $SiO_2$ shell synthesis, surfactants and chloroform are added to a round-bottom flask under sonication. Chloroform solution of functionalized $ZrO_2$ nanoparticle and $NH_4OH$ solution are added slowly to the stirring solution at room temperature. Tetraethoxysilane (TEOS) was added slowly and the resulting solution was stirred at room temperature for 1 to 2 days. The final solution was washed with methanol to remove the surfactant by precipitation and centrifugation. Another strategy to improve reliability is to prepare porous $ZrO_2$ nanoparticles, where the dye molecules are located on the inner surface of pores on the nanoparticle surface.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has" and "having"), "include" (and any form of include, such as "includes" and "including"), and "contain" (and any form contain, such as "contains" and "containing") are open-ended linking verbs. As a result, a method or device that "comprises", "has", "includes" or "contains" one or more steps or elements possesses those one or more steps or elements, but is not limited to possessing only those one or more steps or elements. Likewise, a step of a method or an element of a device that "comprises", "has", "includes" or "contains" one or more features possesses those one or more features, but is not limited to possessing only those one or more features.

As used herein, the terms "comprising" and "including" or grammatical variants thereof are to be taken as specifying the stated features, integers, steps or components but do not preclude the addition of one or more additional features, integers, steps, components or groups thereof. This term encompasses the terms "consisting of" and "consisting essentially of".

The phrase "consisting essentially of" or grammatical variants thereof when used herein are to be taken as specifying the stated features, integers, steps or components but do not preclude the addition of one or more additional features, integers, steps, components or groups thereof but only if the additional features, integers, steps, components or groups thereof do not materially alter the basic and novel characteristics of the claimed composition, device or method.

All publications cited in this specification are herein incorporated by reference as if each individual publication were specifically and individually indicated to be incorporated by reference herein as though fully set forth.

Subject matter incorporated by reference is not considered to be an alternative to any claim limitations, unless otherwise explicitly indicated.

Where one or more ranges are referred to throughout this specification, each range is intended to be a shorthand format for presenting information, where the range is understood to encompass each discrete point within the range as if the same were fully set forth herein.

While several aspects and embodiments of the present invention have been described and depicted herein, alternative aspects and embodiments may be affected by those skilled in the art to accomplish the same objectives. Accordingly, this disclosure and the appended claims are intended to cover all such further and alternative aspects and embodiments as fall within the true spirit and scope of the invention.

The invention claimed is:

1. A phosphor-functionalized nanoparticle comprising:
   an inorganic nanoparticle core;
   surface polymer brushes, including:
      a plurality of long-chain polymers bonded to the surface of the inorganic nanoparticle core, said long-chain polymers each having molecular weight greater than 500; and
      a plurality of short-chain polymers bonded to the surface of the inorganic nanoparticle core, said short-chain polymers each having molecular weight less than 0.5 times the average molecular weight of the long-chain polymers; and
   one or more organic phosphors bonded to at least one of the inorganic nanoparticle core and one or more of the plurality of short-chain polymers,
   wherein graft density of the short-chain polymers on the surface of the inorganic nanoparticle core ($\sigma_{SC}$) is greater than graft density of the long-chain polymers on the surface of the inorganic nanoparticle core ($\sigma_{LC}$).

2. The phosphor-functionalized nanoparticle according to claim 1, wherein said surface polymer brushes have a polydispersity index (PDI) of 1.5 to 2.3.

3. The phosphor-functionalized nanoparticle according to claim 1, wherein the inorganic nanoparticle core has a refractive index greater than 1.95.

4. The phosphor-functionalized nanoparticle according to claim 1, wherein the inorganic nanoparticle core comprises a III-N compound, and/or a metal oxide.

5. The phosphor-functionalized nanoparticle according to claim 4, wherein the inorganic nanoparticle core comprises a metal oxide selected from titanium dioxide ($TiO_2$), indium tin oxide (ITO), and zirconium dioxide ($ZrO_2$).

6. The phosphor-functionalized nanoparticle according to claim 5, wherein the inorganic nanoparticle core comprises $ZrO_2$.

7. The phosphor-functionalized nanoparticle according to claim 1, wherein one or more of the long-chain polymers comprise poly(glycidyl methacrylate) units, polydimethylsiloxane units, poly(dimethylsiloxane-co-diphenylsiloxane) units, poly(methyl methacrylate) (PMMA) units, cyclo-aliphatic polymer units, polyethylene terephthalate (PET) units, polyethylene naphthalate (PEN) units, and/or poly(methylphenylsiloxane) units.

8. The phosphor-functionalized nanoparticle according to claim 1, wherein the long-chain polymers are epoxy compatible or silicone compatible.

9. The phosphor-functionalized nanoparticle according to claim 8, wherein the long-chain polymers comprise poly(glycidyl methacrylate) units, polydimethylsiloxane units, and/or poly(dimethylsiloxane-co-diphenylsiloxane) units.

10. The phosphor-functionalized nanoparticle according to claim 1, wherein at least one of the one or more organic phosphors is bonded to the inorganic nanoparticle core.

11. The phosphor-functionalized nanoparticle according to claim 1, wherein at least one of the one or more organic phosphors is bonded to one of the short-chain polymers.

12. The phosphor-functionalized nanoparticle according to claim 1, wherein said phosphor-functionalized nanoparticle is coated with a silica ($SiO_2$) shell.

13. The phosphor-functionalized nanoparticle according to claim 1, wherein a$\sigma_{SC}$ is greater than three times $\sigma_{LC}$.

14. The phosphor-functionalized nanoparticle according to claim 1, wherein at least one of the one or more organic phosphors comprises a compound or residue thereof, wherein the compound is selected from fluorescein, a fluorone dye, an arylsulfonate dye, and a compound containing a residue of Formula (I):

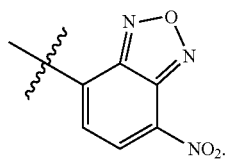

(I)

15. The phosphor-functionalized nanoparticle according to claim 14, wherein at least one of the one or more organic phosphors comprises a compound of Formula (II) or a residue thereof:

(II)

wherein
R$^1$ is selected from —COOH, —C(O)OCH$_2$CCH, and —C(O)OCP(O)(OR$^{2a}$)(OR$^{2b}$); and
R$^{2a}$ and R$^{2b}$ are individually selected from hydrogen and C$_{1-6}$ alkyl.

16. The phosphor-functionalized nanoparticle according to claim 15, wherein at least one of the one or more organic phosphors comprises a compound or residue thereof selected from:

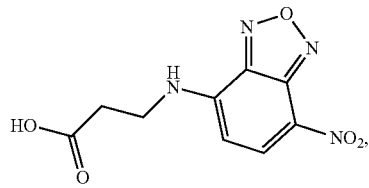

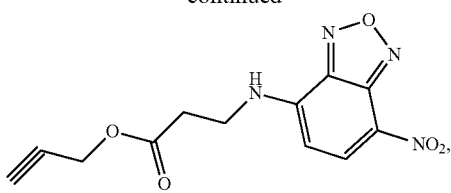

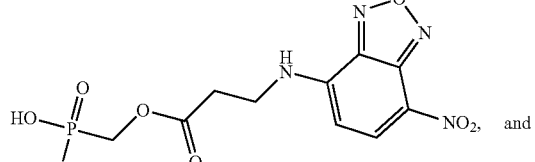

and

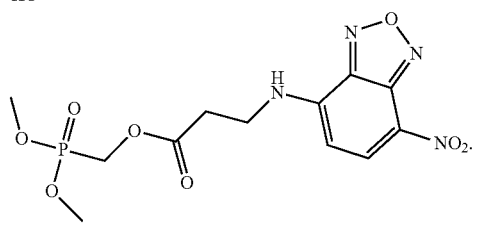

17. A polymer matrix comprising the phosphor-functionalized nanoparticle according to claim 1.

18. The polymer matrix according to claim 17, said polymer matrix comprising poly(glycidyl methacrylate), polydimethylsiloxane, poly(dimethylsiloxane-co-diphenylsiloxane), poly(methyl methacrylate) (PMMA), a cycloaliphatic polymer, polyethylene terephthalate (PET), polyethylene naphthalate (PEN), and/or poly(methylphenylsiloxane).

19. A light-emitting diode (LED) comprising the polymer matrix according to claim 17.

20. An optical system comprising the polymer matrix according to claim 17.

* * * * *

UNITED STATES PATENT AND TRADEMARK OFFICE
CERTIFICATE OF CORRECTION

PATENT NO. : 9,773,953 B2
APPLICATION NO. : 14/781481
DATED : September 26, 2017
INVENTOR(S) : Li et al.

It is certified that error appears in the above-identified patent and that said Letters Patent is hereby corrected as shown below:

On the Title Page

In the Assignee (73): Delete "Rensselaer Polytechnic Institute, Troy, NY (US)" and insert
-- Rensselaer Polytechnic Institute, Troy, NY (US) and University of South Carolina, Columbia, SC (US) --

In the Claims

Column 14, Line 62: Claim 13, Delete "a$\sigma_{SC}$" and insert -- $\sigma_{SC}$ --

Signed and Sealed this
Twenty-eighth Day of November, 2017

Joseph Matal
*Performing the Functions and Duties of the*
*Under Secretary of Commerce for Intellectual Property and*
*Director of the United States Patent and Trademark Office*